US012178978B2

(12) United States Patent
Binner et al.

(10) Patent No.: US 12,178,978 B2
(45) Date of Patent: Dec. 31, 2024

(54) DEVICE AND METHOD FOR APPLICATION OF COSMETIC COMPOSITIONS THROUGH A GRATED END EFFECTOR

(71) Applicant: JOHNSON & JOHNSON CONSUMER INC., Skillman, NJ (US)

(72) Inventors: Curt Binner, Furlong, PA (US); Benjamin Serbiak, Brooklyn, NY (US)

(73) Assignee: JOHNSON & JOHNSON CONSUMER INC., Skillman, NJ (US)

( * ) Notice: Subject to any disclaimer, the term of this patent is extended or adjusted under 35 U.S.C. 154(b) by 968 days.

(21) Appl. No.: 16/947,724

(22) Filed: Aug. 13, 2020

(65) Prior Publication Data

US 2021/0046296 A1 Feb. 18, 2021

Related U.S. Application Data

(60) Provisional application No. 62/888,025, filed on Aug. 16, 2019.

(51) Int. Cl.
*A61M 35/00* (2006.01)
*A61B 5/00* (2006.01)
(Continued)

(52) U.S. Cl.
CPC ......... *A61M 35/003* (2013.01); *A61B 5/0077* (2013.01); *A61M 35/00* (2013.01);
(Continued)

(58) Field of Classification Search
CPC ................ A61M 35/003; A61M 35/00; A61M 2205/52; A61M 2205/8206;
(Continued)

(56) References Cited

U.S. PATENT DOCUMENTS 8,027,505 B2 9/2011 Edgar et al.
8,184,901 B2 5/2012 Edgar et al.
(Continued)

FOREIGN PATENT DOCUMENTS

JP 2005-216131 A 8/2005
KR 20070032493 3/2007
(Continued)

OTHER PUBLICATIONS

Second Office Action mailed on Nov. 5, 2024 in counterpart Chinese patent application No. 202080056616.4, and its English Translation.

*Primary Examiner* — Huy C Ho
(74) *Attorney, Agent, or Firm* — Wan Chieh Lee; Haug Partners LLP

(57) ABSTRACT

A device for applying a composition to a skin of a face includes an end effector having a base portion and a protruding portion extending distally from the base portion. The protruding portion has a distal opening. The device also includes a detector arrangement obtaining image data corresponding to an image of an area of the skin through the distal opening and an applicator arrangement applying the composition to a location within the area. The device further includes a processing arrangement receiving and analyzing the image data to determine whether the applicator is aimed to safely dispense the composition to the area and whether a frexel within the area corresponds to a skin artifact, and directing the applicator to selectively apply the composition to the frexel when the applicator is aimed to safely dispense the composition to the area and the skin artifact is detected from the frexel.

13 Claims, 7 Drawing Sheets

(51) Int. Cl.
*B41J 3/36* (2006.01)
*B41J 3/407* (2006.01)
*B41J 29/393* (2006.01)
*A45D 44/00* (2006.01)
*A61B 90/30* (2016.01)

(52) U.S. Cl.
CPC ............... *B41J 3/36* (2013.01); *B41J 3/4073* (2013.01); *B41J 29/393* (2013.01); *A45D 2044/007* (2013.01); *A61B 5/442* (2013.01); *A61B 2090/309* (2016.02); *A61M 2205/52* (2013.01); *A61M 2205/8206* (2013.01); *A61M 2210/04* (2013.01); *B41J 2203/01* (2020.08)

(58) Field of Classification Search
CPC .. A61M 2210/04; A61B 5/0077; A61B 5/442; A61B 2090/309; B41J 3/36; B41J 3/4073; B41J 29/393; B41J 2203/01; A45D 2044/007; A45D 44/005; A45D 44/00; A45D 34/04; A61K 8/044; A61K 8/29; A61Q 19/00
USPC ........................................................ 328/128
See application file for complete search history.

(56) References Cited

U.S. PATENT DOCUMENTS

| | | |
|---|---|---|
| 9,247,802 B2 | 2/2016 | Edgar |
| 9,462,872 B2 | 10/2016 | Edgar |
| 2007/0035815 A1 | 2/2007 | Edgar et al. |
| 2008/0194971 A1 | 8/2008 | Edgar et al. |
| 2009/0025747 A1 | 1/2009 | Edgar et al. |
| 2011/0124989 A1* | 5/2011 | Edgar .................. A45D 44/005 132/200 |
| 2013/0302078 A1 | 11/2013 | Edgar |
| 2017/0078584 A1 | 3/2017 | Won |
| 2017/0256084 A1 | 9/2017 | Iglehart et al. |
| 2019/0080451 A1 | 3/2019 | Iglehart et al. |
| 2019/0318489 A1 | 10/2019 | Katsuyama |

FOREIGN PATENT DOCUMENTS

| | | | |
|---|---|---|---|
| WO | WO-2016014886 A1 * | 1/2016 | ............. A45D 34/04 |
| WO | 2018/117020 | 6/2018 | |

* cited by examiner

DEVICE AND METHOD FOR APPLICATION OF COSMETIC COMPOSITIONS THROUGH A GRATED END EFFECTOR

PRIORITY CLAIM

This application claims priority to U.S. Provisional Application Ser. No. 62/888,025 filed Aug. 16, 2019, the entire contents of which is hereby incorporated by reference herein.

BACKGROUND OF THE INVENTION

Cosmetic compositions can be applied by manually spreading the composition across the skin of the face with fingers, brushes or sponges. Alternatively, certain specialized liquid formulations of cosmetics can be applied to the skin using an airbrush device where the cosmetic is applied as a pressurized spray onto the skin of a subject. These airbrush devices are generally manually directed by a user across the skin of the subject, which can include sensitive regions (e.g., eyes, nostrils and/or mouth) that may be irritated or harmed by application of such a pressurized spray of cosmetic. The pressurized airbrush cosmetic spray may not be safe for use in proximity to the eyes of the subject because the user may not be able to control the airbrush device with sufficient precision to avoid accidentally dispensing the pressurized spray of cosmetic into the eyes, which may irritate or even damage the fragile structure of the eyes. In addition, cosmetic compositions often include particulate materials suspended in a liquid formulation. Although such particulate materials may be safe for use topically, they may not be safe if inhaled, ingested or applied to mucus membranes. For example, commonly used cosmetic particulate materials, such as, for example, micronized particulates, may be safe for use in liquid topical formulations, such as lotions and/or creams, but may be hazardous if dispensed in a manner that leads to inhalation through the nostrils or ingestion via the mouth. Because a user may not be able to control an airbrush device precisely enough to avoid accidentally dispensing the pressurized spray of cosmetic into the nostrils or mouth, these devices may present health risks when used in proximity to the nostrils and mouth.

BRIEF SUMMARY OF THE INVENTION

One exemplary embodiment of the present invention is directed to a handheld device for applying a composition to a skin of a face of user. The device comprises an end effector comprising a base portion and a protruding portion extending distally from the base portion, the protruding portion having a distal opening. The device also comprises a detector arrangement configured to obtain image data corresponding to an image of an area of the skin through the distal opening of the end effector. The device further comprises an applicator arrangement configured to apply the composition to a location within the area of the skin. In some embodiments, the applicator arrangement comprises a nozzle configured to dispense a pressurized pulse of the composition from a reservoir to form a thin layer of the composition on the skin. For example, the composition may be a cosmetic composition comprising particles of a reflectance modifying agent (e.g., titanium dioxide) in a liquid suspension. Additionally, the device comprises a processing arrangement configured to receive the image data from the detector arrangement, analyze the image data to determine whether the applicator arrangement is aimed to safely dispense the composition to the area of skin and whether a frexel within the area of skin corresponds to a skin artifact, and direct the applicator arrangement to selectively apply the composition to the frexel when the applicator arrangement is aimed to safely dispense the composition to the area of skin and the skin artifact is detected from the frexel. In some embodiments, the processing arrangement may determine whether the skin artifact is detected from the frexel based on a reflectance of the area of skin detected in the image.

In some embodiments, the processing arrangement of the handheld device may be configured to direct the applicator arrangement to withhold from application of the composition to the skin when the applicator arrangement is not safely aimed to dispense the composition to the area of skin. The processing arrangement may also analyze the image data and determine the applicator arrangement to be aimed to safely dispense the composition to the area of skin when the image data corresponds to a region on the face of the user located at least a predetermined distance away from at least one of eyes, nostrils and mouth of the face of the user. Furthermore, the processing arrangement may analyze the image data to determine a tilt of the device. In particular, the processing arrangement may determine the applicator arrangement to be aimed to safely dispense the composition to the area of skin when a magnitude of the tilt of the device is below a predetermined threshold, and determines the applicator arrangement as not safely aimed to dispense the composition to the area of skin when magnitude of the tilt of the device is above the predetermined threshold.

The protruding portion of the end effector may further comprise a plurality of grating bars extending across the distal opening, and the image data corresponds to an image of the area of skin overlaid with the plurality of grating bars. The processing arrangement may be configured to analyze the image data to identify a shadow of at least one of the grating bars in the image and determining a length of the shadow based on the image data. The processing arrangement may be further configured to determine the applicator arrangement to be aimed to safely dispense the composition to the area of skin when the length of the shadow is below a predetermined threshold, and determine the applicator arrangement as not safely aimed to dispense the composition to the area of skin when the length of the shadow is above the predetermined threshold. The processing arrangement may be also configured to adjust the image data to substitute data for portions of the image corresponding to the grating bars with data generated by the processing arrangement that approximate for skin underlying the grating bars, and to analyze the adjusted image data to identify locations within the area of skin that correspond to skin artifacts.

A method for application of a composition to a skin of a face a user is also provided. The method comprises obtaining, by a detector arrangement, image data corresponding to an image of an area of the skin over which a device is placed. For example, the image data corresponds to an image of the area of skin overlaid with a plurality of grating bars of an end effector of the device, the grating bars extending across the area of the skin. The method also comprises analyzing, by a processing arrangement, the image data to determine a tilt of the device as compared to the area of the skin. The method further comprises determining, by the processing arrangement, whether an applicator arrangement is aimed to safely dispense the composition to the area of skin based on the tilt of the device. The method further comprises analyzing, by the processing arrangement, the image data to identify locations within the area of skin that correspond to skin artifacts, and also selectively applying, by the applicator arrangement, the composition to the identified locations only when the applicator arrangement is determined to be aimed to safely dispense the composition to the area of skin. In some embodiments, the processing arrangement identifies locations within the area of skin that correspond to skin artifacts based on a reflectance of the area of skin detected in the image.

In some embodiments, the processing arrangement may determine the applicator arrangement to be aimed to safely dispense the composition to the area of skin when a magnitude of the tilt of the device is below a predetermined threshold, and determine the applicator arrangement as not safely aimed to dispense the composition to the area of skin when magnitude of the tilt of the device is above the predetermined threshold. For example, the processing arrangement may determine the tilt of the device by analyzing the image data to identify a shadow of at least one of the grating bars in the image and analyzing the shadow to determine a three-dimensional vector corresponding to the tilt. Furthermore, the processing arrangement may adjust the image data to substitute data for portions of the image corresponding to the grating bars with data generated by the processing arrangement that approximate for skin underlying the grating bars and analyze the adjusted image data to identify locations within the area of skin that correspond to skin artifacts.

These and other aspects of the invention will become apparent to those skilled in the art after a reading of the following detailed description of the invention, including the figures and appended claims.

DETAILED DESCRIPTION OF THE INVENTION

Figure 1:
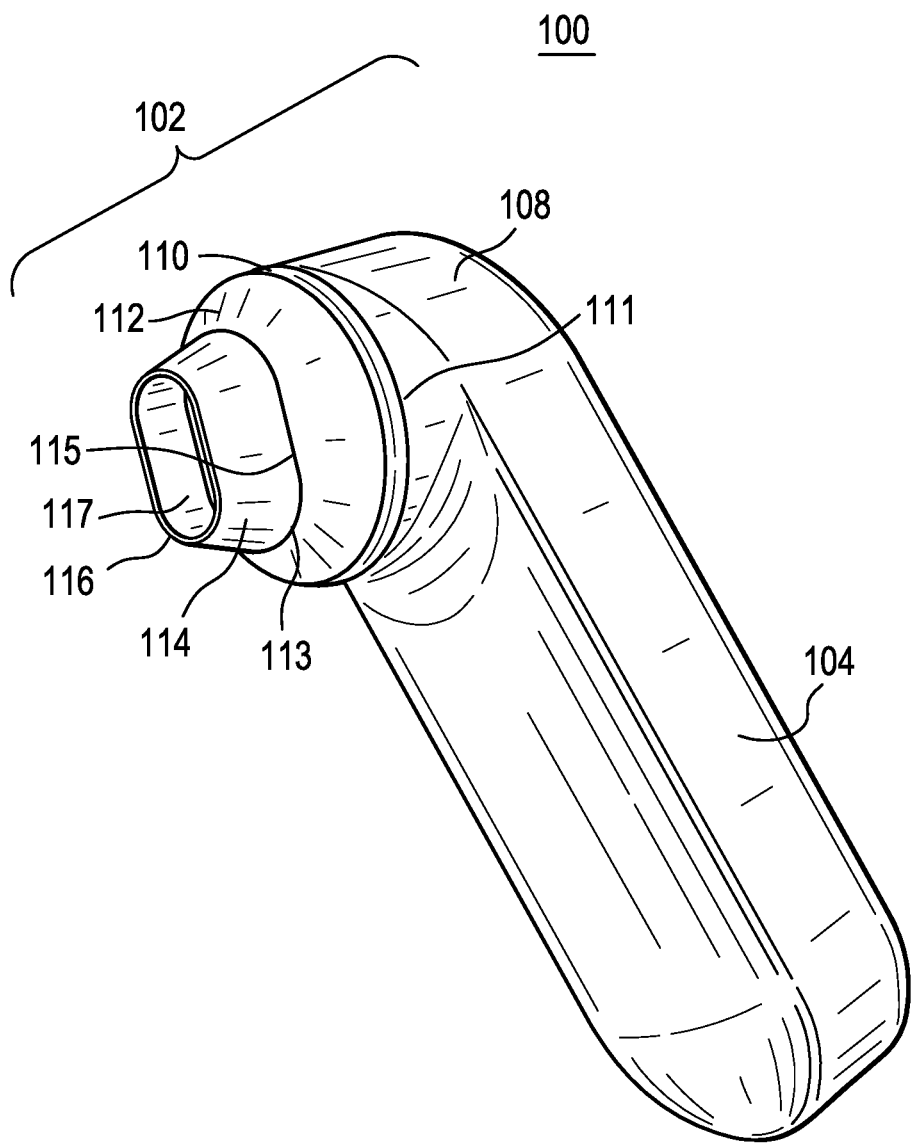
FIG. 1 show a perspective view of a device for applying a composition to the skin of a user, according to an exemplary embodiment of the present application.

The present invention relates to devices and methods for applying a composition onto skin, in particular, skin of the face of a mammal or a human. More specifically, the invention relates to devices and methods for selectively applying a topical composition to the skin of the face to, for example, enhance aesthetic appearance of the skin, and which provides improved safety for operating near sensitive regions (e.g., eyes, nostrils and/or mouth) on the face of the mammal or human.

The present disclosure may be further understood with reference to the following description and the appended drawings, wherein like elements are referred to with the same reference numerals. It should be noted that the terms "proximal" and "distal," as used herein are intended to refer to a direction toward (proximal) and away from (distal) a user of the device.

The term "frexel" as used herein refers to a small pixel-like region of skin, which corresponds to a single large pixel or a small number of pixels in a digitally obtained image. For example, a frexel may correspond to a skin area having an average diameter from about $\frac{1}{15}$ to about $\frac{1}{5}$ inch.

The term "middle spatial frequencies" as used herein is explained further below. For example, image data corresponding to an image of the skin can capture light reflectances extending over a range of spatial frequencies, which measures the level of detail present in an image over a distance across the skin observed by a detector (e.g., a camera) that generates the image data. Spatial frequency may be measured by the number of periodic features, e.g., described as a periodic sine-wave pattern corresponding to cycles of alternating dark and light striped patterns, within an image over a distance across the skin observed by the detector. The spatial frequency of an image may be calibrated and/or normalized based on a distance from which the skin is imaged by the detector. It is noted that spatial frequency, as used herein, does not measure a wavelength or color of light, but instead refers to a spatial wavelength of the structure of the details of the skin captured by the detector in the image. Data corresponding to an image in a spatial domain (e.g., in the form of pixels or frexel) can be processed by a computer processor using a Fourier transform function to obtain data for the image in the spatial frequency domain. This spatial frequency domain relates to an optical resolution of the image captured, which is distinct from a wavelength or color of light. As would be understood by those skilled in the art, the spatial frequency components of the image may generally be separated into three different categories, including (1) high spatial frequencies, (2) middle spatial frequencies, and (3) low spatial frequencies, using any suitable methods for image analysis, e.g., Fourier transform, filtering, etc. As would be understood by those skilled in the art, spatial frequency components having high spatial frequencies correspond to light reflectance in the image that contribute to the appearance of sharp edges and small details within the image. For example, for an image of skin, the spatial frequency components having high spatial frequencies correspond to features that appear to be small, natural variations in the skin, such as those derived from the genetic code of the person, e.g., pores, hair, follicles, cells, iris of the eye, etc. Low spatial frequencies correspond to light reflectances in the image that contribute to the broad visual appearance such as, for example, the color of larger features such as, for example, the nose, cheeks, etc. The remaining spatial frequency components between the low and spectral frequencies are referred to as the middle spatial frequencies.

The range of middle spatial frequencies may be determined relative to the image captured. For example, the range of middle spatial frequencies for an area of facial skin may be different from the range of middle spatial frequencies for an area of the skin on a leg. The range of middle spatial frequencies may also depend on the underlying skin tone of the skin imaged. In one example, the middle spatial frequencies for human skin can range from about 0.03 cycles/mm to about 1.5 cycles/mm, or more specifically from about 0.05 cycles/mm to about 1.0 cycles/mm and, even more specifically, from about 0.07 cycles/mm to about 0.5 cycles/mm.

The present application provides a device and method for selectively applying a composition to skin, in particular, skin of the face of a subject (e.g., a mammal or a human) while providing improved safety for operation near sensitive regions (e.g., eyes, nostrils, and/or mouth) that may not otherwise be safe and/or suitable for application of the composition. More particularly, the present application provides a device and method for selectively applying a topical composition to the skin of the face while providing safeguards that restrict application of the composition into such sensitive regions. As described above, some compositions may be suitable for topical application but may not be suitable for direct application into sensitive areas such as, for example, the eyes, the nose and/or the mouth. Therefore, operation of the device of the present application near such sensitive areas (e.g., within a predetermined range of a border of a sensitive region) is restricted to improve safety of operation of the device near such sensitive regions. As another example, if a composition suitable for topical application is not suitable for inhalation, operation of the device near inlets to the respiratory system (i.e., the nose and mouth) may be restricted. For example, the device and method of embodiments of the present application analyze data corresponding to an image or one or more frames of images of an area of skin adjacent to which the device is positioned to determine whether an applicator arrangement of the device is aimed to safely dispense the composition to the area of skin (e.g., whether the applicator arrangement is aimed to apply the composition outside of the predetermined range of a border of a sensitive region), and when the applicator arrangement is determined to be aimed to safely dispense the composition to the area of skin, further analysis of the image data is performed to selectively apply the composition to selected portions of the skin to address skin artifacts (e.g., scars, wrinkles, blemishes, freckles, sun damage, age spots etc.) whose appearance the user wishes to minimize or eliminate to improve an over-all aesthetic appearance of the skin. The device prevents application of the composition by the applicator arrangement when the applicator arrangement is determined to be aimed to dispense the composition in an unsafe manner (e.g., to an area of skin that is within the predetermined range of a border of a sensitive region).

Figure 2:
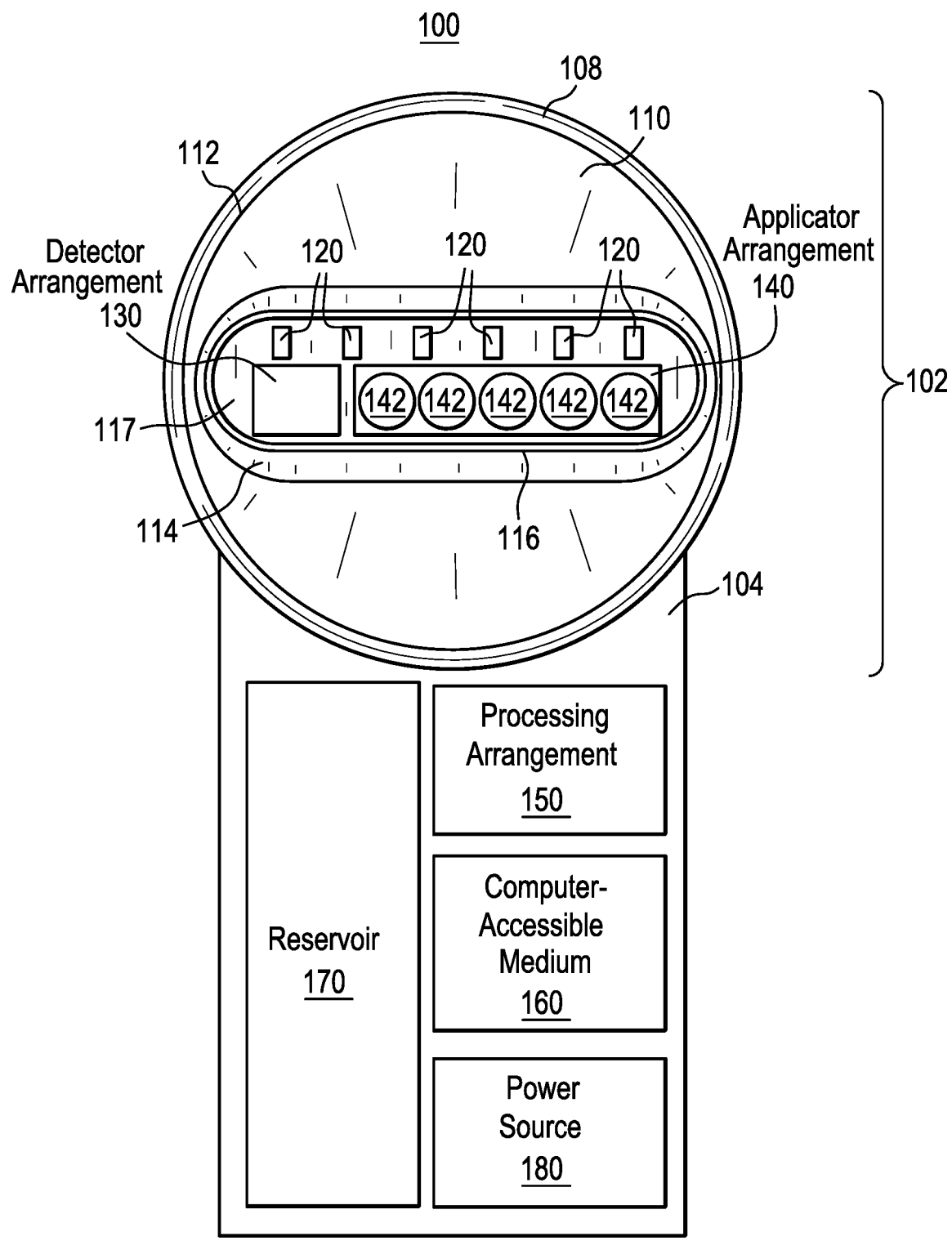
FIG. 2 shows a block diagram of the exemplary device of FIG. 1 for applying a composition to the skin of a user.

FIGS. 1 and 2 show an exemplary embodiment of a device 100 for applying a composition (e.g., a cosmetic or medical composition) to the skin. The device 100 of this embodiment is preferably sized and shaped to be a handheld device 100 designed to be held within a palm of a user's hand. The device 100 according to this embodiment comprises a head portion 102 and a handle portion 104. The handle portion 104 of the device 100 has an elongated shape defining a cavity for housing components therein. In some embodiments, the handle portion 104 is sized and shaped to be held within the palm of the user's hand. In other embodiments, the handle portion 104 is sized and shaped to be held by the fingertips of the user's hand.

The head portion 102 of the device 100 according to this embodiment comprises an end effector 110 that is reversibly attached to a body 108 of the head portion 102. The end effector 110 includes interior surfaces that define a cavity therein through which light can be delivered and an image of an area of skin can be captured by a detector arrangement. In certain embodiments, the interior surfaces of the end effector 110, in particular, the interior surfaces of the protruding portion 114, are surface modified (e.g., a textured mold finish) and/or treated with a surface coating (e.g., a light absorbing coating) to reduce reflectance of light by the modified or treated surfaces. In the exemplary embodiment shown in FIGS. 1 and 2, the end effector 110 comprises a base portion 112 that is reversibly attached to the body 108 and a protruding portion 114 that extends distally from the base portion 112. In certain embodiments, the base portion 112 and the protruding portion 114 of the end effector 110 may be formed as a single unitary component, such as, for example, molded as a single piece of plastic. In some embodiments, the end effector 110 may be a disposable component that can be replaced after a session of use, or as desired by the user. The base portion 112 of the end effector 110 shown in FIGS. 1 and 2 extends from a proximal end 111 that is reversibly attached to the body 108 and a distal end 113 that is connected to the protruding portion 114. As shown in the exemplary embodiment of FIG. 1, the base portion 112 can have a tapered shape such that its proximal end 111 is wider (e.g., has a greater cross-sectional area) than its distal end 113. In particular, the tapered shape of the base portion 112 may be a funnel shape or a conoid shape. The proximal end 111 of the base portion 112 may comprise any suitable engagement mechanism for reversibly engaging and disengaging from the body 108 as would be understood by those skilled in the art. For example, the proximal end 111 of the base portion 112 and the body 108 may comprise complementary threading to reversibly engage and disengage from one another. In another example, the proximal end 111 of the base portion 112 may be frictionally fitted to the body 108. In a further embodiment, the proximal end 111 of the base portion 112 and the body 108 may include complementary interlocking mechanisms that can be pushed together to frictionally engage and disengage the end effector 110 from the body 108. Furthermore, in some embodiments, the base portion 112 may have a circular cross-sectional shape and rotatable about a longitudinal axis extending from its proximal end 111 to its distal end 113 to reversibly engage and disengage from the body 108. In other embodiments, the base portion 112 is rotationally locked with respect to the body 108 when the base portion 112 lockingly attached to the body 108.

The protruding portion 114 of the end effector 110 extends from a proximal end 115 that is connected to the base portion 112 to a distal end 116 defining a distal opening 117 in the end effector 110. In one exemplary embodiment, the protruding portion 114 extends from its proximal end 115 to its distal end 116 along a longitudinal axis that is perpendicular or substantially perpendicular to a plane extending across the proximal end 111 of the base portion 112 of the end effector 110. The protruding portion 114 may also have a tapered shape where the proximal end 115 is wider than the distal end 116. As shown in FIGS. 1 and 2, the proximal and distal ends 115, 116 of the protruding portion 114 can have elongated, in particular, oval cross-sectional shapes. However, it is contemplated that the proximal and distal ends 115, 116 of the protruding portion 114 may have any suitable shape for imaging and selectively applying a composition therethrough to an area of skin, as will be discussed further below.

In some embodiments, the protruding portion 114 of the end effector 110 may include additional surface features. In one exemplary embodiment, the distal end 116 of the end effector 110 comprises a plurality of ridges or protrusions extending distally therefrom such that, when the end effector 110 is held against the skin, only the protrusions extending distally from the distal end 116 of the end effector 110 contact the skin. These protrusions reduce overall contact area of the device 100 with the skin and this may, for example, prevent smearing of previously applied composition, improve comfort and/or reduce pillowing of the surface of the skin that might otherwise result if a user pushed an end effector not including such protrusions against the skin.

Figure 3:
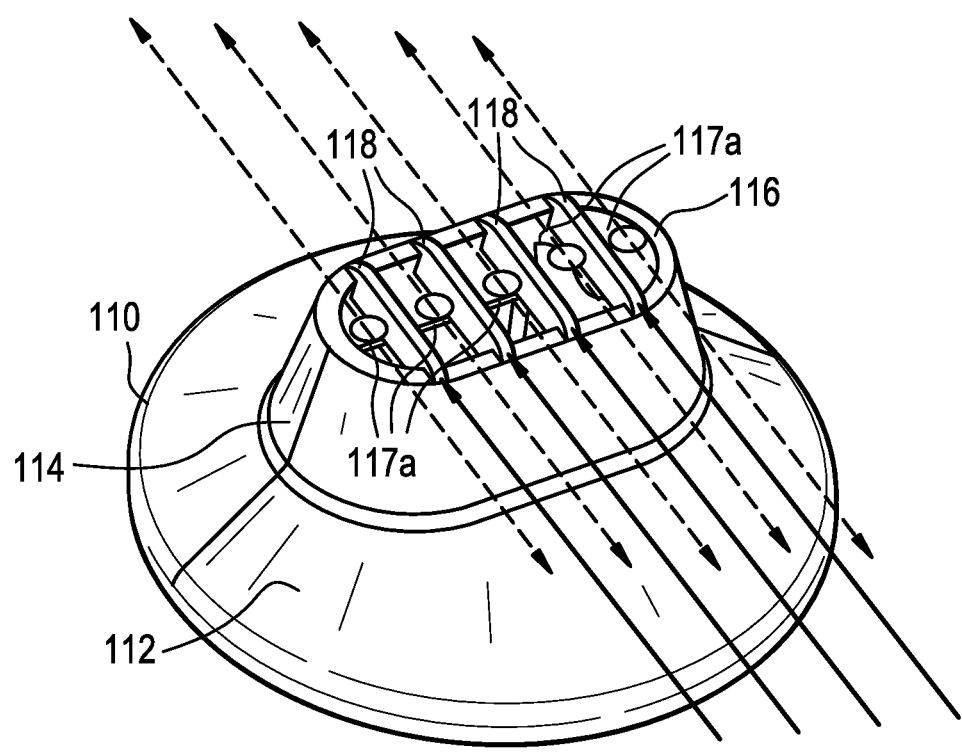
FIG. 3 shows an exemplary embodiment of an end effector of a device for applying a composition to the skin of a user, according to an exemplary embodiment of the present application.

In one particular embodiment, as shown in FIG. 3, the distal end 116 of the end effector 110 includes a plurality of grating bars 118 (which is shown in the drawings with solid arrows), extending across a width of the distal opening 117 of the end effector 110. The grating bars 118 divide the distal opening 117 of the end effector 110 into a plurality of distal opening segments 117a where the applicator arrangement 140 includes at least one nozzle 142 associated with each segment 117a. Thus, each segment 117a may be independently analyzed to identify portions of skin to which the composition is to be applied and, based on this analysis, operating the nozzle 142 associated with the corresponding segment 117a. Each of the distal opening segments 117a, shown in FIG. 3, includes a dot illustrating alignment of at least one nozzle 142 of the applicator arrangement 140 within each distal opening segment 117a. As can be seen in FIG. 3, the grating bars 118 extend distally from the distal end 116 of the end effector 110 such that, when the end effector 110 is held against the skin, only the grating bars 118 are in contact with the skin. In this embodiment, the plurality of grating bars 118 all extend distally from the distal end 116 by the same distance such that the grating bars 118 collectively lie along a plane parallel or substantially parallel to the distal opening 117 of the end effector 110. In another embodiment, the grating bars 118 are aligned along the same plane as the distal opening 117 such that, when the end effector 110 is held against the skin, the grating bars 118 as well as the distal end 116 of the end effector 110 are in contact with the skin. As shown in FIG. 3, the grating bars 118 are parallel or substantially parallel to one another. The plurality of grating bars 118 in this embodiment are spaced evenly or substantially evenly from one another. Furthermore, the grating bars 118 in some embodiments are surface treated or modified to reduce friction as they are moved along the skin. For example, friction between the grating bars 118 and the skin may be reduced by coating the grating bars 118 with a friction-reducing coating, such as, for example, perfluoropolyether (PFPE), Polytetrafluoroethylene (PTFE), Nylon, Acetel, Polyester, polyimide, polyether ether ketone (PEEK), etc. Alternatively, the grating bars 118 may be formed from a material having reduced coefficient of friction, such as, for example, those materials identified above.

Figure 4:
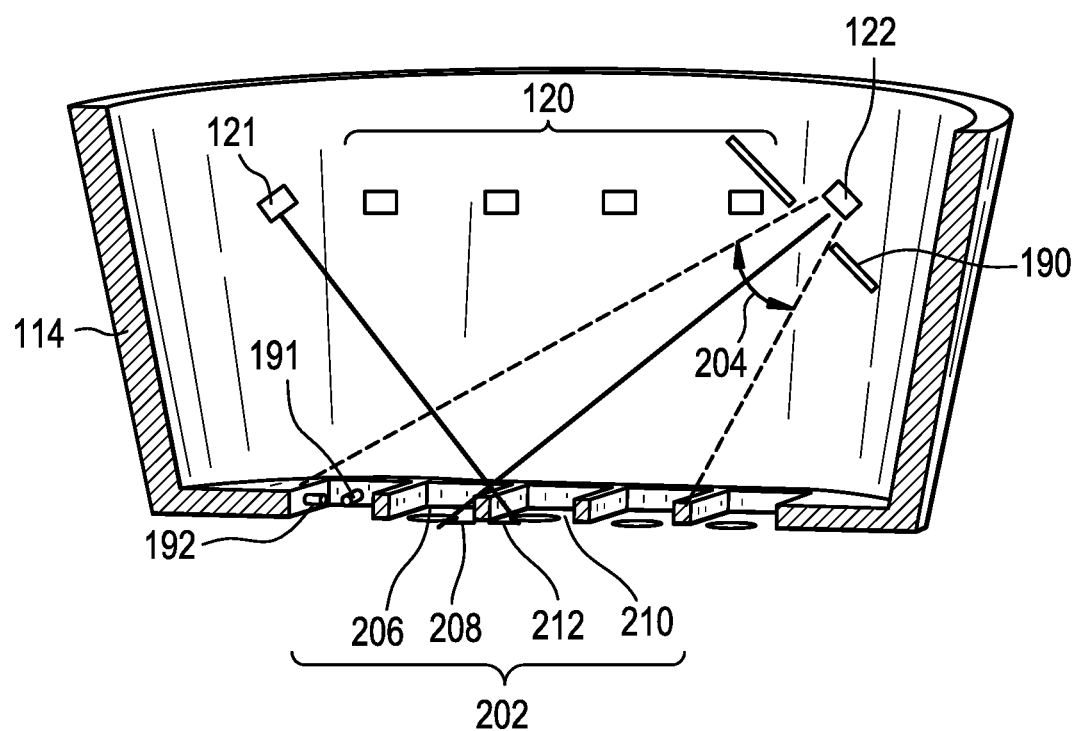
FIG. 4 shows an exemplary embodiment of a protruding portion of an end effector of a device for applying a composition to the skin of a user, according to an exemplary embodiment of the present application.

In addition, the distal end 116 of the end effector 110 of this embodiment further comprises a pair of shadow guide pins 191, 192 (two are shown in FIG. 4, more than two may be included) extending along the same plane as the grating bars 118. The first pin 191 is perpendicular or substantially perpendicular to the second pin 192. This pair of shadow guide pins 191, 192 casts two-direction shadows onto the area of skin framed by the distal opening 117 when this area of skin is illuminated by light source(s) 120, 121, 122 from the body 108 of the head portion 102. The two-direction shadows may then be captured in an image or one or more frames of images by a detector arrangement 130. In particular, the two-direction shadows casted by the shadow guide pins 191, 192 may be used to define two of three axes in a three-dimensional coordinate space for determining an orientation of the device 100 captured in the image(s) and/or a tilt of at least a portion of the device 100. The tilt may be determined as a directional vector in three-dimensional space having a magnitude indicating an amount of deviation from an orientation of the surface of the skin.

The body 108 of the head portion 102 according to this embodiment comprises at least one light source 120, 121, 122 for delivering light (e.g., visible light) through the distal opening 117 of the end effector 110 to an area of skin. The at least one light source 120, 121, 122 may comprise any suitable light emitting device for illuminating the area of skin, for example, one or more light emitting diodes (LEDs). The at least one light source 120, 121, 122 may also be selected and arranged to provide an amount of illumination over the area of skin sufficient to detect and/or measure reflectance of light by the skin. In embodiments in which a plurality of grating bars 118 extend through the distal opening 117 of the end effector 110, as shown in FIG. 3, a portion of the area of skin may be shadowed by the grating bars 118 while the light source(s) 120, 121, 122 provides a substantially uniform distribution of light to the remaining portion of the area of skin. In certain embodiments, a portion of the area of skin may also be shadowed by outer edges of the protruding portion 114 of the end effector 110, in particular, along a length of the protruding portion 114 while the light source(s) 120, 121, 122 provides a substantially uniform distribution of light to the remaining portion of the area of skin.

Preferably, the light source(s) 120, 121, 122 are arranged to deliver light through the distal opening 117 of the end effector 110 to an area of skin, without providing significant illumination to an interior of the end effector 110. For example, the light source(s) 120 may be positioned perpendicular to the distal opening 117 of the end effector 110. More particularly, the light source(s) 120 may be positioned perpendicular or substantially perpendicular to areas of interest within the area of the skin framed by the distal opening 117 of the end effector 110, when the device 100 is in use. As another example, the light source(s) 121, 122 may be angled to direct light through the distal opening 117, while minimizing light directed toward interior surfaces of the end effector 110. In particular, the light source(s) 122 may be angled to direct light within a radial cone 204 (illustrated by the dotted lines in FIG. 4) through the distal opening 117 to an area of interest 202 on the skin within the area of the skin over which the distal opening 117 is place. It is contemplated that additional physical barriers and/or reflectors 190 may also be included in the body 108 of the head portion 102 to direct light from the light source(s) 121 or 122 to desired areas of interest while minimizing the reflectance of light from the interior surfaces of the end effector 110.

In some embodiments, the body 108 of the head portion 102 comprises at least two different light sources 121, 122 for delivering light at two different wavelengths, which may be operated sequentially or simultaneously. The at least two different light sources 121, 122 may be utilized simultaneously to provide different functionality. The two different wavelengths may be selected to minimize interference between illumination from these two different light sources 121, 122. For example, the body 108 may comprise a first light source 121 delivering light having a first color (e.g., blue light) and a second light source 122 delivering light having a second color (e.g., green light). The first and second light sources 121, 122 may be utilized by the device 100 to illuminate the area of skin for imaging and analysis to ascertain different properties of the imaged area. For example, the first light source 121 may be used by the device 100 to illuminate the area of skin for imaging and analysis to determine a tilt or a positioning of the device 100 relative to an orientation of the surface of the skin, e.g., whether outer edges of the protruding portion 114 of the end effector 110 or grating bars 118 adjacent to each distal opening segment 117a are in contact with the surface of the skin. In particular, the first light source 121 may be selected to provide illumination for shadow casting and maximizing the contrast of shadows. The second light source 122 may, for example, be used to illuminate the area of skin for imaging and analysis to identify skin artifacts. In one exemplary embodiment, the second light source 122 may provide diffuse lighting suitable for image analysis for detection of skin artifacts corresponding to locations having intense contributions in the middle spatial frequencies of an image. The first and second light sources 121, 122 may be operably connected to a processing arrangement 150 to selectively operate and control the first and second light sources 121, 122, as will be discussed further below.

The body 108 of the head portion 102 also comprises a detector arrangement 130 for obtaining image data corresponding to an image or one or more frames of images of an area of skin obtained through the distal opening 117 of the end effector 110. In embodiments where a plurality of grating bars 118 extend through the distal opening 117 of the end effector 110, as shown in FIG. 3, the image data may correspond to an image or one or more frames of images of an area of skin over which the distal opening 117 is placed overlaid with the grating bars 118. The detector arrangement 130 comprises at least one sensor detecting light reflected from the area of the skin and/or the grating bars 118. As would be understood by those skilled in the art, the sensor(s) may comprise any suitable components for detecting reflectance of light. For example, the sensor(s) may be sensitive to an amount of reflected light in one or more wavelengths. Suitable sensors may include, for example, photographic or video cameras (which may include different types of camera lenses), photodiodes and/or phototransistors as would be understood by those skilled in the art. In one exemplary embodiment, the sensor(s) of the detector arrangement 130 may comprise an RGB camera which can detect light in red, green and blue channels of the camera. In some embodiments, the detector arrangements 130 may further comprise a color filter array (e.g., a Bayer filter) for obtaining image data corresponding to images in different wavelengths (e.g., in different colors) when two or more light source(s) 121, 122 each having a different wavelength are used.

The light source(s) 120, 121, 122 and the detector arrangement 130 are operably connected to a processing arrangement 150 executing instructions stored on a computer-accessible medium 160. The processing arrangement 150 in this embodiment controls the light source(s) 120, 121, 122 and receives and analyzes image data received from the detector arrangement 130. It is contemplated that the processing arrangement 150 and the computer-accessible medium 160 may be positioned anywhere within or external to the device 100. In one embodiment, as shown in FIG. 1, the processing arrangement 150 and the computer-accessible medium 160 are located within the handle portion 104. The processing arrangement 150 in this embodiment also controls an applicator arrangement 140 to selectively apply the composition to desired frexels within areas of the skin when the processing arrangement 150 determines that the applicator arrangement 140 is aimed to safely dispense the composition to the areas of skin. The processing arrangement 150 may be, e.g., entirely or a part of, or include, but is not limited to, a computer/processor that can include, e.g., one or more microprocessors, and use instructions stored on a computer-accessible medium 160 (e.g., memory storage device). The computer-accessible medium 160 may, for example, be a non-transitory computer-accessible medium containing executable instructions therein. A storage arrangement may be provided separately from the computer-accessible medium 160, which may provide the instructions to the processing arrangement 150 to configure the processing arrangement 150 to execute certain exemplary procedures, processes and methods.

As shown in FIG. 2, the applicator arrangement 140 of this embodiment is part of the body 108 of the head portion 102. The applicator arrangement 140 of this embodiment selectively applies the composition to portions of the skin as directed by the processing arrangement 150 based on image data from the detector arrangement 130. The applicator arrangement 140 according to this embodiment comprises at least one suitable application device for depositing a topical composition, (e.g., a cosmetic composition) onto one or more frexels at which artifacts have been identified. An exemplary cosmetic application device in this embodiment includes, for example, a sprayer (e.g., an electronic sprayer or airbrush sprayer), a drop control device, or any other suitable application device for applying a composition in small drops to identified frexels as would be understood by those skilled in the art. In one exemplary embodiment, the applicator arrangement 140 comprises one or more nozzle(s) 142 for depositing a pressurized liquid or viscous composition in the form of a pressurized pulse or mist onto the skin to form a thin layer of cosmetic coverage at an identified frexel. The nozzle(s) 142 dispense the composition in the form of pulse or mist droplets onto a surface of skin and thereby forming a thin continuous or discontinuously layer of the composition on the skin. In certain embodiments, the applicator arrangement 140 comprises multiple nozzles 142, such as, for example, an array of nozzles arranged in any desired configuration. The use of multiple nozzles 142 increases an overall rate at which the device 100 may apply the composition to frexels, reducing a total amount of time a user will need to move the device 100 across a targeted portion of skin before the desired level of treatment of artifacts has been achieved. For example, the applicator arrangement 140 may include 3 to 8 nozzles, or 4 to 6 nozzles, each nozzle being aimed differently so that the composition can be applied to multiple frexels or different parts of a frexel at the same time. In one exemplary embodiment, the applicator arrangement 140 includes 5 nozzles. In embodiments where a plurality of grating bars 118 extend through the distal opening 117 of the end effector 110, as shown in FIG. 3, the applicator arrangement 140 may comprise one or more nozzles 142 aimed to dispense the composition to each distal opening segment 117a.

The nozzle 142 may be any suitable device for depositing a thin layer of the cosmetic composition onto the skin. In one exemplary embodiment, the nozzle 142 comprises dual chambers with a first chamber holding the liquid or viscous composition and a second chamber containing a propellant (e.g., compressed air or nitrogen gas) applying pressure to, but not mixed with the composition when a pulse of the composition is dispensed to a frexel. In another example, the nozzle 142 comprises a first chamber holding the liquid or viscous composition and a second chamber containing a propellant to be mixed with the cosmetic composition when a pulse of the composition is dispensed to a frexel. Although two exemplary embodiments of the nozzle 142 are described above, it is contemplated that the device of the present application may include any suitable nozzle(s) 142 for dispensing droplets of the composition under pressure as would be understood by those skilled in the art.

The applicator arrangement 140 is operably connected to a reservoir 170 containing the cosmetic composition to be applied to the skin. In particular, the applicator arrangement 140 is fluidly connected by a series of conduits, valves, and/or pressure sources to the reservoir 170. It is contemplated that the reservoir 170 may be housed anywhere within the device 100. In one exemplary embodiment, as shown in FIG. 2, the reservoir 170 is housed within the handle portion 104 of the device 100. The composition within the reservoir 170 is transferred from the reservoir 170 to the applicator arrangement 140 for deposition of the composition. In some embodiments, the reservoir 170 is a removeable container that can be replaced upon exhaustion of the contents therein. For example, the reservoir 170 may be a pressurized canister containing the composition to be applied to the skin therein.

The composition to be applied to the skin may comprise, for example, any suitable cosmetic ingredients for modifying an appearance of the skin, such as, for example, an opaque substance, a tinted cosmetic, or any other suitable compositions for enhancing the appearance of skin. The composition may also comprise ingredients such as a moisturizer for hydration, a carrier, or a benefit agent (e.g., a beneficial compound/composition/extract or an active ingredient) for treating and/or ameliorating a skin condition, e.g., acne, hyperpigmentation, eczema, hives, vitiligo, psoriasis, rosacea, warts, shingles, cold sore, pigmentation and tone, redness/oxidative skin stress, wrinkles, brightening, sagging/elasticity, etc. The exemplary composition in this embodiment is a cosmetic composition applied to the skin to alter or minimize the appearance of an artifact based on the image data supplied by the detector arrangement 130. Exemplary embodiments of benefit agents that may be incorporated into the composition are further described below.

A non-limiting list of useful hydrating active benefit agents includes hyaluronic acid, and humectants. The hyaluronic acid may be linear, cross-linked, or a mixture of linear and cross-linked hyaluronic acid. It may be in a salt form, such as sodium hyaluronate. A humectant is a compound intended to increase the water content of the top layers of skin (e.g., hygroscopic compounds). Examples of suitable humectants include, but are not limited to, glycerin, sorbitol or trehalose or a salt or ester thereof.

A non-limiting list of useful benefit agents for acne includes benzoyl peroxide, retinoids including retinol, retinal, retinoic acid, retinyl acetate, and retinyl palmitate, hydroxy acids include, but are not limited, to glycolic acid, lactic acid, malic acid, salicylic acid, citric acid, and tartaric acid, sulfur, Zinc PCA (Zinc Pyrrolidone carboxylic acid), Allantoin (5-ureidohydantoin), Rosemary, 4-hexylresorcinol, N-acetyl glucosamine, gluconolactone, niacinamide, azelaic acid, and resveratrol.

A non-limiting list of useful pigmentation active benefit agents includes resorcinols, such as niacinamide, 4-hexyl resorcinol, curcuminoids (such as Sabiwhite (Tetrahydrocurcumin), phytic acid, resveratrol, soybean *Glycine soja* oil, gluconolactone, azelaic acid, and retinoids including retinol, retinal, retinoic acid, retinyl acetate, and retinyl palmitate, enzymes such as laccase, tyrosinase inhibitors, melanin-degradation agents, melanosome transfer inhibiting agents including PAR-2 antagonists, exfoliants, sunscreens, retinoids, antioxidants, Tranexamic acid, tranexamic acid cetyl ester hydrochloride, skin bleaching agents, linoleic acid, adenosine monophosphate disodium salt, *Chamomilla* extract, allantoin, opacifiers, talcs and silicas, zinc salts, and the like. Examples of suitable tyrosinase inhibitors include but, are not limited to, Vitamin C and its derivatives, Vitamin E and its derivatives, Kojic Acid, Arbutin, resorcinols, hydroquinone, Flavones e.g., Licorice flavanoids, Licorice root extract, Mulberry root extract, *Dioscorea coposita* root extract, Saxifraga extract and the like, Ellagic acid, Salicylates and derivatives, Glucosamine and derivatives, Fullerene, Hinokitiol, Dioic acid, Acetyl glucosamine, 5,5'-dipropyl-biphenyl-2,2'-diol (Magnolignan), 4-(4-hydroxyphenyl)-2-butanol (4-HPB), combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4-alkyl-resorcinols such as 4-butyresorcinol (rucinol), 4-hexylresorcinol, phenylethyl resorcinol, 1-(2,4-dihydroxyphenyl)-3-(2, 4-dimethoxy-3-methylphenyl)-Propane and the like and natural extracts enriched in resorcinols. Examples of salicylates include, but are not limited to, 4-methoxy potassium salicylate, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative A non-limiting list of useful redness/antioxidant active benefit agents includes water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, propolis and extracts of feverfew. By "extracts of feverfew," it is meant extracts of the plant "*Tanacetum parthenium*," One particularly suitable feverfew extract is commercially available as about 20% active feverfew.

A non-limiting list of useful wrinkle active benefit agents includes N-acetyl glucosamine, 2-dimethylaminoethanol, copper salts such as copper chloride, peptides like argireline, syn-ake and those containing copper, coenzyme Q10, dill, blackberry, princess tree, *Picia anomala*, and chicory, resorcinols, such as 4-hexyl resorcinol, curcuminoids and retinoids including retinol, retinal, retinoic acid, retinyl acetate, and retinyl palmitate, hydroxy acids include, but are not limited, to glycolic acid, lactic acid, malic acid, salicylic acid, citric acid, and tartaric acid.

A non-limiting list of useful brightening active benefit agents includes Vitamin C and its derivatives such as Ascorbic Acid 2-Glucoside, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid.

A non-limiting list of useful benefit agents for sagging skin includes blackberry extracts, cotinus extracts, feverfew extracts, extracts of *Phyllanthus niruri* and bimetal complexes having copper and/or zinc constituents. The bimetal complex having copper and/or zinc constituents may be, for example, copper-zinc citrate, copper-zinc oxalate, copper-zinc tartarate, copper-zinc malate, copper-zinc succinate, copper-zinc malonate, copper-zinc maleate, copper-zinc aspartate, copper-zinc glutamate, copper-zinc glutarate, copper-zinc fumarate, copper-zinc glucarate, copper-zinc polyacrylic acid, copper-zinc adipate, copper-zinc pimelate, copper-zinc suberate, copper-zinc azealate, copper-zinc sebacate, copper-zinc dodecanoate, or combinations thereof.

Additional skin benefit agents or actives may include those actives listed in the following paragraphs. While some of these actives may have been listed above, they are included below to ensure a more robust listing.

Examples of suitable additional benefit agents include: skin lightening agents, darkening agents, anti-aging agents, tropoelastin promoters, collagen promoters, anti-acne agents, shine control agents, anti-microbial agents such as anti-yeast agents, anti-fungal, and anti-bacterial agents, anti-inflammatory agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, hair growth enhancing agents, hair growth delaying agents, firming agents, hydration boosters, efficacy boosters, anti-callous agents, agents for skin conditioning, anti-cellulite agents, fluorides, teeth whitening agents, anti-plaque agents, and plaque-dissolving agents, odor-control agents such as odor masking or pH-changing agents, and the like. Examples of various suitable additional cosmetically acceptable actives include UV filters such as but not limited to avobenzone (Parsol 1789), bis-disulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octrylene, oxybenzone (Eusolex 4360), sulisobenzone, bisoctrizole (Tinosorb M), titanium dioxide, zinc oxide, carotenoids, free radical scavengers, spin traps, retinoids and retinoid precursors such as retinol, retinoic acid and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, amino acids such a proline, vitamins, lactobionic acid, acetyl-coenzyme A, niacin, riboflavin, thiamin, ribose, electron transporters such as NADH and FADH2, and other botanical extracts such as oat, aloe vera, Feverfew, Soy, Shiitake mushroom extracts, and derivatives and mixtures thereof.

Examples of suitable skin lightening benefit agents include, but are not limited to, tyrosinase inhibitors, melanin-degradation agents, melanosome transfer inhibiting agents including PAR-2 antagonists, exfoliants, sunscreens, retinoids, antioxidants, Tranexamic acid, tranexamic acid cetyl ester hydrochloride, skin bleaching agents, linoleic acid, adenosine monophosphate disodium salt, *Chamomilla* extract, allantoin, opacifiers, talcs and silicas, zinc salts, and the like.

Examples of suitable tyrosinase inhibitors include but, are not limited to, Vitamin C and its derivatives, Vitamin E and its derivatives, Kojic Acid, Arbutin, resorcinols, hydroquinone, Flavones e.g. Licorice flavanoids, Licorice root extract, Mulberry root extract, *Dioscorea coposita* root extract, Saxifraga extract and the like, Ellagic acid, Salicylates and derivatives, Glucosamine and derivatives, Fullerene, Hinokitiol, Dioic acid, Acetyl glucosamine, 5,5'-dipropyl-biphenyl-2,2'-diol (Magnolignan), 4-(4-hydroxyphenyl)-2-butanol (4-HPB), combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4-alkyl-resorcinols such as 4-butyresorcinol (rucinol), 4-hexylresorcinol (Synovea HR, Sytheon), phenylethyl resorcinol (Symwhite, Symrise), 1-(2,4-dihydroxyphenyl)-3-(2,4-dimethoxy-3-methylphenyl)-Propane (nivitol, Unigen) and the like and natural extracts enriched in resorcinols. Examples of salicylates include, but are not limited to, 4-methoxy potassium salicylate, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative. In more preferred embodiments, the tyrosinase inhibitor comprises Phenylethyl resorcinol, 4-hexyl resorcinol, or ascorbyl-2-glucoside.

Examples of suitable melanin-degradation agents include, but are not limited to, peroxides and enzymes such as peroxidases and ligninases. In certain preferred embodiments, the melanin-inhibiting agents include a peroxide or a ligninase.

Examples of suitable melanosome transfer inhibiting agents including PAR-2 antagonists such as soy trypsin inhibitor or Bowman-Birk Inhibitor, Vitamin B3 and derivatives such as Niacinamide, Essential soy, Whole Soy, Soy extract. In certain preferred embodiments, the melanosome transfer inhibiting agents includes a soy extract or niacinamide.

Examples of exfoliants include, but are not limited to, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid, and mechanical exfoliation such as microdermabrasion. In certain preferred embodiments, the exfoliant include glycolic acid or salicylic acid.

Examples of sunscreens include, but are not limited to, avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, and the like.

Examples of retinoids include, but are not limited to, retinol (Vitamin A alcohol), retinal (Vitamin A aldehyde), retinyl acetate, retinyl propionate, retinyl linoleate, retinoic acid, retinyl palmitate, isotretinoin, tazarotene, bexarotene, Adapalene, combinations of two or more thereof and the like. In certain preferred embodiments, the retinoid is selected from the group consisting of retinol, retinal, retinyl acetate, retinyl propionate, retinyl linoleate, and combinations of two or more thereof. In certain more preferred embodiments, the retinoid is retinol.

Examples of antioxidants include, but are not limited to, water-soluble antioxidants such as sulfhydryl compounds and their derivatives (e.g., sodium metabisulfite and N-acetyl-cysteine, glutathione), lipoic acid and dihydrolipoic acid, stilbenoids such as resveratrol and derivatives, lactoferrin, iron and copper chelators and ascorbic acid and ascorbyl acid derivatives (e.g., ascobyl-2-glucoside, ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinones. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, black tea, white tea, pine bark, feverfew, parthenolide-free feverfew, oat extracts, blackberry extract, cotinus extract, soy extract, pomelo extract, wheat germ extract, Hesperedin, Grape extract, *Portulaca* extract, Licochalcone, chalcone, 2,2'-dihydroxy chalcone, *Primula* extract, propolis, and the like.

In some preferred embodiments, useful benefit agents for acne include, but are not limited, salicylic acid, Zinc PCA (Zinc Pyrrolidone carboxylic acid), Allantoin (5-ureido-hydantoin), Rosemary, 4-hexylresorcinol, N-acetyl glucosamine, gluconolactone, niacinamide, azelaic acid, and resveratrol.

In some preferred embodiments, a list of useful pigmentation active benefit agents includes tetrahydrocurcumin, phytic acid, resveratrol, soybean *Glycine soja* oil, gluconolactone, laccase, 4-hexyl resorcinol, N-acetyl glucosamine, gluconolactone, niacinamide, azelaic acid, and resveratrol.

In some preferred embodiments, a list of useful active benefit agents includes to simultaneously treat acne and pigmentation includes 4-hexyl resorcinol, N-acetyl glucosamine, gluconolactone, niacinamide, azelaic acid, and resveratrol.

In one particular embodiment, the composition comprises one or more reflectance modifying agents (RMAs) (any component useful for altering reflectance of the skin). For example, suitable RMAs may include inks, dyes, pigments, bleaching agents, chemically altering agents and other substances that may be used to alter the reflectance of the skin. Some suitable RMAs may include a transparent RMA, such as a dye or a diluted pigment. Other suitable RMAs may include an opaque RMA having high refractive index particles. In particular, the high refractive index particles may comprise particles having a refractive index of 2.0 or greater. In one specific example, the RMA may comprise particles of titanium dioxide. For example, the RMA may comprise particles of titanium dioxide having an average diameter from about 0.35 microns to about 1.35 microns, from about 0.5 microns to about 1.0 microns, or from about 0.6 microns to about 0.8 microns. Specifically, the titanium dioxide particles may be uniformly distributed and/or suspended in the cosmetic composition (e.g., a liquid suspension).

The device 100 according to this embodiment further comprises a power source 180 providing power to control and operate the device 100. It is contemplated that the power source 180 may be located anywhere within the device 100 or may alternatively be external to the device 100. In one exemplary embodiment, as shown in FIG. 2, the power source 180 which is housed within the handle portion 104 of the device 100, is operably connected to the light source(s) 120, 121, 122 the detector arrangement 130, the applicator arrangement 140 and/or the processing arrangement 150. Those skilled in the art will understand that various known suitable sources of power may be used. For example, the power source 180 may comprise a battery or a connection to an external source of power. In particular, the power source 180 may comprise a rechargeable battery device.

In use, the head portion 102 is placed over an area of skin to be treated. In particular, the distal opening 117 of the end effector 110 is placed against the skin to frame an area that is to be imaged by the detector arrangement 130 and selectively treated by the applicator arrangement 140 as directed by the processing arrangement 150. During use, the device 100 images a plurality of different areas of skin. For example, as the head portion 102 is moved across a surface of the skin, the device 100 continuously or serially images different areas of the skin to obtain image data and analyze the image data to identify select frexels to which the composition is applied. More particularly, as the user moves the head portion 102 back and forth across the surface of the skin in multiple passes, the device 100 reviews previously treated areas to detect artifacts which were missed or incompletely addressed and applies the composition to identified artifacts on the skin (i.e., to select frexels). Where a plurality of grating bars 118 extend through the distal opening 117 of the end effector 110, the user may prefer to move the device 100 along a path parallel or substantially parallel to the grating bars 118, as shown by the dotted lines in FIG. 3.

Figure 5:
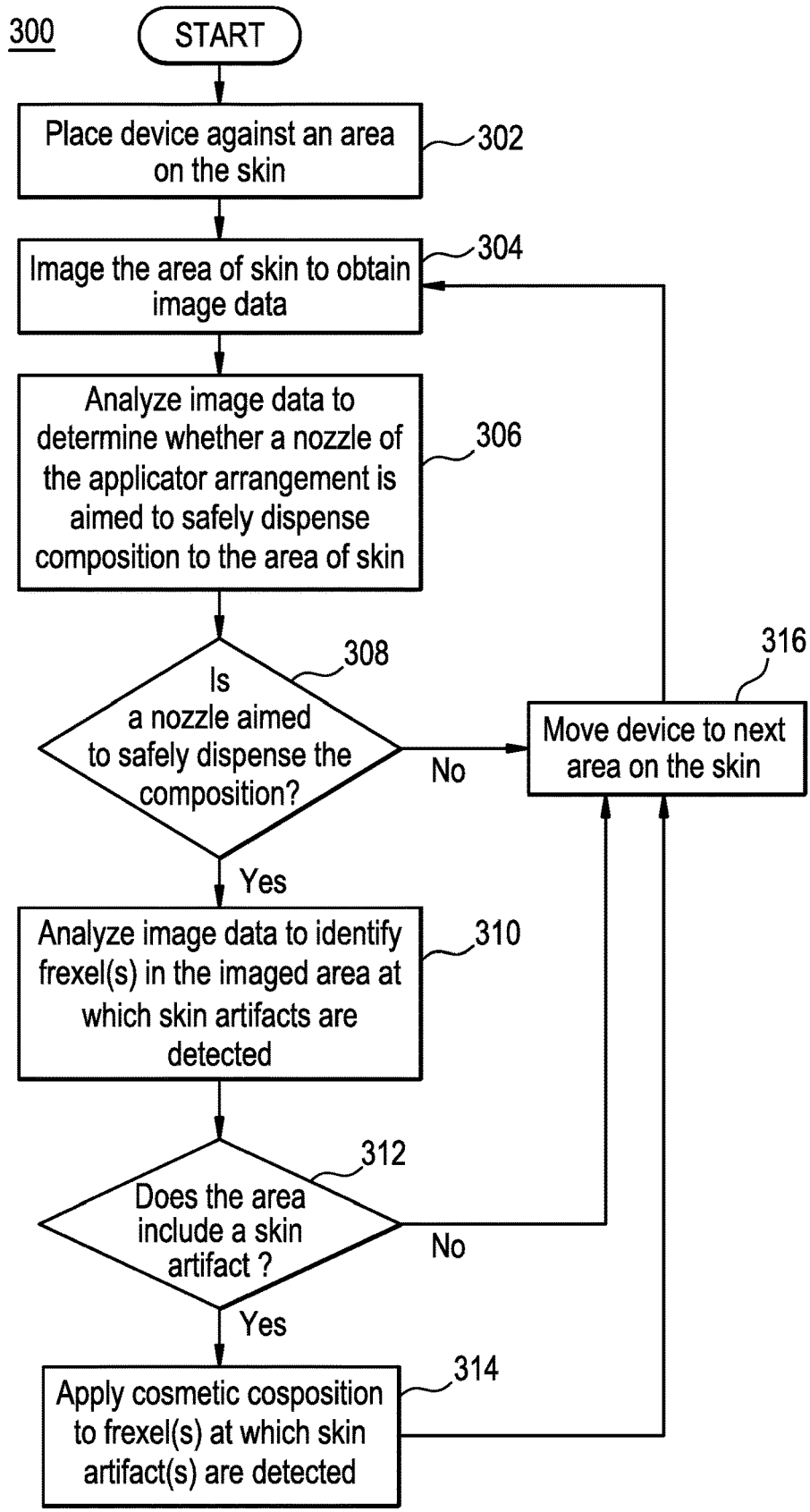
FIG. 5 shows an exemplary method for applying a cosmetic composition to the skin of a user, according to an exemplary embodiment of the present application.

The present application also includes a method for determining whether at least a portion of an applicator arrangement 140 of a device 100 is safely positioned and aimed toward a target area of skin to selectively apply a composition (e.g., a cosmetic composition) to locations (e.g., frexels) within the area of skin. Dispensing is permitted by the application arrangement 140 (or by certain nozzles of the application arrangement 140) only when the applicator arrangement 140 or certain ones of its nozzles is determined to be aimed safely and is prevented (the applicator arrangement 140 is disabled) when the applicator arrangement 140 is determined to be aimed to dispense the composition in an unsafe or potentially unsafe manner. An exemplary method 300 is shown in FIG. 5. In step 302, the user initiates use of the device 100 by placing the distal end 106 of the end effector 110 of the device 100 against a surface of skin, for example, the skin of the face. The distal opening 117 of the end effector 110 frames an area of skin that is imaged and analyzed by the device 100. In some embodiments, as described above, the distal opening 117 may be divided by a plurality of grating bars 118 into a plurality of distal opening segments 117*a* where at least one nozzle 142 of the applicator arrangement 140 is aimed to apply cosmetic to skin over which each distal opening segment 117*a* is positioned. As indicated in step 304, the detector arrangement 130 images the area through the distal opening 117 to obtain image data for the area of the skin.

In steps 306 and 308, the image data is analyzed by the processing arrangement 150 to first determine whether the nozzle(s) 142 associated with each distal opening segment 117*a* is aimed to safely dispense the composition to skin. Each nozzle 142 of this embodiment may be assessed and controlled independently from each other. Those nozzles 142 that are determined to be unsafely positioned are disabled while the remaining nozzles 142 of the applicator arrangement 140 are permitted to continue operations. These determinations may be conducted using any number of suitable methods, as will be discussed further below.

For example, the processing arrangement 150 may analyze the image data to determine whether image data for an area of skin over which a distal opening segment 117*a* is placed also corresponds to a region on the face of the user outside a predetermined distance or radius from one or more sensitive regions (e.g., eyes, nostrils and/or mouth). If the area of skin is outside of the predetermined distance or radius from the one or more sensitive regions, the processing arrangement 150 in this embodiment determines that the nozzle(s) 142 associated with this distal opening segment 117*a* is aimed to safely dispense the composition to the skin. Alternatively, if the area of skin is within a sensitive region or within the predetermined distance or radius from a sensitive region (i.e., near to or including one or more of the sensitive regions), the processing arrangement 150 determines that the nozzle(s) 142 associated with the distal opening segment 117*a* is not aimed to dispense the composition safely. In particular, the processing arrangement 150 of this embodiment compares the image data for the area of skin over which the distal opening segment 117*a* is placed to a database of previously acquired image data mapped to regions of the face of the user to identify a region on the face corresponding to the image data and determines whether this region contains a sensitive region or a portion of skin less than a predetermined distance from a sensitive region. In this embodiment, when the processing arrangement 150 determines that a nozzle 142 is not aimed to safely dispense the composition, the processing arrangement 150 disables the unsafely aimed nozzle 142. The processing arrangement 150 may subsequently resume functionality to those disabled nozzle(s) 142 if the device 100 is moved to a different position on the skin and that the processing arrangement 150 subsequently determines that the new positioning of the previously disabled nozzle(s) 142 analyzes is now aimed to safely dispense the composition to the skin.

In another embodiment, the processing arrangement 150 may analyze the image data to determine whether nozzle(s) 142 aimed at an area of skin over which a distal opening segment 117*a* is positioned to safely dispense the composition to the skin. Each distal opening segment 117*a* may be assessed independently from each other and the nozzle(s) 142 associated with each distal opening segment 117*a* may be separately controlled. In particular, the processing arrangement 150 may analyze the portion of the image data corresponding to the area of skin over which a distal opening segment 117*a* is positioned to determine whether a portion of the outer edges of the protruding portion 114 of the end effector 110 and/or grating bars 118 adjacent to the distal opening segment 117*a* is in contact with the surface of the skin. If a portion of the outer edge of the protruding portion 114 or a grating bar 118 that is adjacent to the distal opening segment 117*a* is determined to not be in contact with the surface of the skin, then the processing arrangement 150 determines that the nozzle(a) 142 associated with the analyzed distal opening segment 117*a* is not aimed to safely dispense the composition to the skin and disables the unsafely positioned nozzle(s) 142.

It is noted that the contours of a face of a human are particularly curved around certain of the sensitive regions, such as, for example, areas surrounding the nose adjacent to the eyes, nostrils, and mouth. As a user attempts to address these areas, the surface of the skin may curve away from portions of the outer edges of the protruding portion 114 of the end effector 110 and/or grating bars 118 when the device 100 is placed over these sensitive regions. The detection of a shadow casted by at least a portion of the outer edges of the protruding portion 114 of the end effector 110 and/or one or more of the grating bars 118 adjacent to the distal opening segment 117*a* in the image data may be indicative that the portion of the outer edges of the protruding portion 114 of the end effector 110 and/or the one or more of the grating bars 118 are not positioned to be fully in contact with the surface of the skin, suggesting that the distal opening segment 117*a* may be placed over a sensitive region or within a predetermined distance or radius from the sensitive region. For example, the processing arrangement 150 may disable a nozzle 142 of the applicator arrangement 140 when shadow(s) of the outer edges of the protruding portion 114 and/or one or more of the grating bars 118 is detected in the portion of the captured image corresponding to the distal opening segment 117*a* associated with the nozzle 142. Therefore, the processing arrangement 150 may determine that image data demonstrating a nozzle 142 having such proximity to a sensitive region indicates that the nozzle 142 is aimed to dispense composition in an unsafe manner. The processing arrangement 150 may further analyze a direction and/or a length of the shadow(s) casted by the outer edges of the protruding portion 114 and/or one or more of the grating bars 118 adjacent to the distal opening segment 117*a* to determine whether nozzle(s) 142 associated with the distal opening segment 117*a* is aimed to safely dispense the composition to the skin. In particular, the direction and/or length of the shadows may be used to determine whether the outer edges of the protruding portion 114 and/or one or more of the grating bars 118 adjacent to the distal opening segment 117*a* is separated from the surface of the skin above a certain predetermined tolerance (in either direction and/or length of the shadow) so as to cause the processing arrangement 150 to disable the nozzle(s) 142 associated with the distal opening segment 117*a* to prevent dispensing of the composition near or to sensitive regions. In one exemplary embodiment, the processing arrangement 150 may determine that the nozzle 142 is aimed to safely dispense the composition to the area of skin when a length of a shadow detected therein is below a predetermined threshold, and may determine that the nozzle 142 is aimed to dispense the composition in an unsafe manner when the length of the shadow is above the predetermined threshold.

In a further embodiment, the processing arrangement 150 may determine a tilt of the device 100 relative to the skin by analyzing the image data. Based on the tilt of the device, the processing arrangement 150 determines whether the nozzles 142 of the applicator arrangement 140 are aimed to safely dispense the composition to the skin. As a user attempts to address these areas, the device 100 may be tilted beyond a threshold level increasing a risk that, were composition to be dispensed, the eventual landing point of that composition is less accurately determinable and, as the device 100 in such circumstances is often near sensitive regions, the detection of tilt above a certain predetermined level causes the processing arrangement 150 to disable the applicator arrangement 140 to prevent the composition from entering sensitive regions. The processing arrangement 150 may also take into account a direction of tilt in determining whether the applicator arrangement 140 is aimed unsafely with respect to a sensitive region. For example, the processing arrangement 150 may disable the applicator arrangement 140 when 1) the image data indicates that the device 100 is tilted in a direction that follows contours of a sensitive region; 2) the device 100 is tilted to a degree beyond a predetermined threshold; and/or has a tilt vector magnitude exceeding a predetermined threshold. Therefore, the processing arrangement 150 may determine that image data demonstrating such proximity to a sensitive region indicates that the nozzles 142 of the applicator arrangement 140 are aimed to dispense composition in an unsafe manner. In one exemplary embodiment, the processing arrangement 150 may determine that the applicator arrangement 140 is aimed to safely dispense the composition to the area of skin when the vector magnitude of the tilt of the device is below a predetermined threshold, and may determine that the applicator arrangement 140 is aimed to dispense the composition in an unsafe manner when the vector magnitude of the tilt of the device is above the predetermined threshold.

Furthermore, the processing arrangement 150 may also determine that the applicator arrangement 140 is aimed to dispense the composition in an unsafe manner when the image data demonstrates that the nozzle(s) 142 of the applicator arrangement 140 are misaligned (e.g., separate from the surface of the skin or tilted beyond a particular configuration) such that the nozzle(s) 142 are aimed to deposit composition inaccurately—i.e., when a position on the skin to which the composition would be directed by a nozzle 142 cannot be determined within a desired margin of error from target locations (e.g., frexels). The processing arrangement 150 may disable the nozzle(s) 142 when it determines the potential deviation of composition application from target locations exceed a desired margin of error as higher margins of error may result in unsafe application of the composition to sensitive regions. Therefore, the processing arrangement 150 may disable the nozzle(s) 142 when the image data demonstrates that the nozzle(s) 142 are misaligned to a degree beyond a predetermined threshold and/or when a tilt vector magnitude exceeds a predetermined threshold that may result in erroneous deposition of the composition to non-targeted locations.

In step 308, the processing arrangement 150 evaluates whether at least one nozzle 142 of the applicator arrangement 140 is aimed to safely dispense the composition to an area of skin, after which the method 300 proceeds to step 310 in which the image data is further analyzed to identify locations within the area of skin to which the composition should be applied, (e.g., frexels at which skin artifacts are detected) to alter the visual appearance of the skin. If the processing arrangement 150 determines, based on the image data, that the nozzle(s) 142 is aimed to dispense the composition in an unsafe manner, then the nozzle(s) 142 is prevented from dispensing the composition until this condition has altered, enhancing safety of the device 100 when operating near the eyes, nostrils and/or mouth. More specifically, if the processing arrangement 150 determines that the nozzle(s) 142 is aimed to operate in an unsafe manner, the processing arrangement 150 directs the nozzle(s) 142 to prevent application of the composition to the skin until the device has been moved to align the nozzle(s) 142 to safely dispense the composition to a target area of skin, e.g., aimed at a location away from the sensitive regions and/or positioned with a lower degree of tilt.

In step 310, the processing arrangement 150 analyzes the image data to determine whether locations (e.g., frexels), if any, within the imaged area of skin correspond to skin artifacts. In particular, the processing arrangement 150 analyzes the image data and identifies those locations with the imaged area of skin that correspond to skin artifacts. More particularly, the processing arrangement 150 analyzes the image data to determine whether frexels within the imaged area of skin contain skin artifacts having a magnitude warranting the application of the cosmetic composition (i.e., a magnitude greater than a predetermined threshold level). As would be understood by those skilled in the art, the image data can be analyzed by the processing arrangement 150 using any suitable methods, to identify skin artifacts. For example, image data may be analyzed by the processing arrangement 150 to identify frexel(s), if any, within the imaged area that represent skin artifacts whose appearances should be altered by comparing reflectances corresponding to the frexels captured by the detector arrangement 130 to an average reflectance of the entire area of skin. In one exemplary embodiment of step 310, a frexel identified as having a reflectance that significantly deviates from an average reflectance of the entirety of its associated imaged area is determined to correspond to a skin artifact. In another exemplary embodiment, at least one frexel within the imaged area of skin is analyzed by the processing arrangement 150 to determine whether image data corresponding to the frexel includes spectral components within the range of middle spatial frequencies for the entire frame of skin imaged (i.e., the image obtained by the detector arrangement in step 304) that have an elevated intensity relative to the balance of the image. Locations at which an intensity in the middle spatial frequencies is above a threshold level are identified as artifacts to which the composition should be applied. Preferably, the range of middle spatial frequencies is determined for each area of skin based on a reflectance of the entire imaged area across the skin of the face.

Those frexels that include intense contributions in the middle spatial frequencies of an image may, for example, include artifacts whose appearance a user may wish to alter or minimize. The middle spatial frequencies are believed to contribute a small percentage (e.g., around 5%) to the overall spatial frequency of an image of skin and/or visual perception of the skin. However, it is believed that spatial frequency components within the middle spatial frequencies are particularly visually noticeable and therefore, provide disproportionally larger contribution to the perceived aesthetic appearance of the skin. Therefore, it is believed that altering or minimizing the appearance of skin by selectively applying a cosmetic to those frexels corresponding to details within the middle spatial frequencies of an image of the skin would impart an aesthetic pleasing appearance to the skin. It may be particularly beneficial to selectively alter or minimize the appearance of only those frexels that correspond to middle spatial frequencies to provide a visually noticeable aesthetic change to the appearance of skin while modifying only a limited number of frexels on the skin. Therefore, a reduced amount of cosmetic composition may be applied to the skin while still providing an aesthetically noticeable improvement to the appearance of skin. Additional devices and methods for detecting artifacts using reflectance and analysis of middle spatial frequencies are described in, for example, U.S. Pat. Nos. 8,007,062, 9,020,184 and 10,092,082, the disclosures of which are incorporated by reference herein.

If a skin artifact is detected in step 312, then the methods proceeds to step 314. In step 314, the processing arrangement 150 directs select nozzle(s) 142 of the applicator arrangement 140 to apply to apply the composition to the locations or frexels of the artifact(s) identified within an imaged area of skin. The select nozzle(s) 142 are those that the processing arrangement 150 has determined to be aimed to safely dispense the composition to the skin. Step 312 applies the composition to those locations or frexels from which skin artifacts are detected only when the corresponding nozzle(s) 142 is determined by the processing arrangement 150 to be aimed to safely dispense the composition to the skin. When the processing arrangement 150 determines that the nozzle(s) 142 is aimed to apply the composition to the skin in an unsafe manner, the processing arrangement 150 directs the nozzle(s) 142 to withhold from dispensing the composition. If a skin artifact is not detected in step 312, the method 300 does not apply any composition to any location within the imaged area of skin and the method 300 proceeds to step 316.

In step 316, the device 100 is moved by the user to a new frame or area of the skin and the process is repeated. This movement may be detected by the device 100 by any suitable means, such as, for example, an accelerometer or image analysis. The method 300 then returns to step 304 and continues the method 300 on a new area of skin in the same manner described above. It is noted that the method 300 may be interrupted and terminated by the user before any one of steps 304 through 316 by any suitable operation, such as, for example, removing the device 100 from the skin or switching off the device 100, in particular, the power source 180 of the device.

In a further embodiment, the device 100 comprises an end effector 110 having a plurality of grating bars 118 extending through a distal opening 117 of the end effector 110, such as, for example, shown in FIG. 3. The grating bars 118 of the end effector 110 provide visual guides within the image(s) captured by the detector arrangement 130 useful for determining a tilt of the device 100 relative to the skin, which can then be used in image analysis to determine whether the applicator arrangement 140 is aimed to safely dispense the composition to a target area of skin (steps 306 and 308). In particular, the device 100 in this embodiment analyzes image data corresponding to an image or one or more frames of images of an area of skin obtained through a grated end effector 110 to determine whether the applicator arrangement 140 is aimed to safely dispense the composition to the imaged area of skin. More particularly, the image data obtained by the detector arrangement 130 in this embodiment corresponds to an image or one or more frames of images of an area of skin over which the distal opening 117 is placed that is also overlaid with the grating bars 118. The processing arrangement 150 analyzes the image data to determine whether the nozzle(s) 142 of the applicator arrangement 140 is aimed to safely dispense the composition to the skin. For example, the processing arrangement 150 in this embodiment analyzes the image data to identify at least one shadow cast by at least one of the grating bars 118 and/or by an outer edge of the protruding portion 114 of the end effector 110 and determines a tilt of the nozzle(s) 142 relative to the surface of the skin based on a length, width and/or shape of the shadow. In one embodiment, the tilt may be quantitatively measured using a length of the shadow. Specifically, if the length of the shadow is above a predetermined threshold, the applicator arrangement 140 is determined to be aimed to dispense the composition in an unsafe manner to the area of skin. If the length of the shadow is below the predetermined threshold, the applicator arrangement 140 is determined to be aimed to safely dispense the composition to the area of skin. In another embodiment, the tilt of the nozzle(s) relative to the surface of the skin may be quantitatively measured using a ratio of two different shadows, as will be discussed further below.

Figure 6:
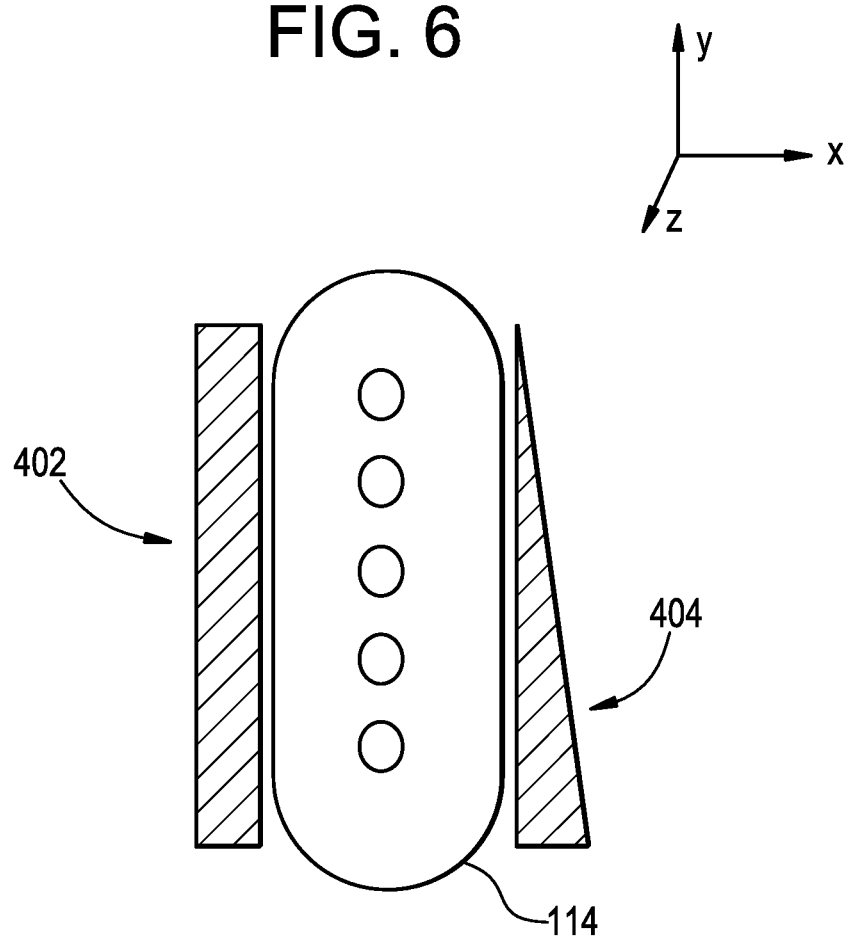
FIG. 6 shows an exemplary embodiment of a view from an interior a protruding portion of an effector of a device in a distal direction towards the skin of a user, according to an exemplary embodiment of the present application.

As discussed above, the tilt of each of the nozzles or the device as a whole may also be determined as a directional vector in three-dimensional space having a magnitude indicating an amount of deviation from the surface of the skin. The directional vector may be a composite of directional components in each of x, y, and z directions as shown in FIG. 6. FIG. 6 shows a view from an interior of the head portion 102 of the device 100 in a distal direction through the distal opening 117 of the end effector 110, including a plurality of dots illustrating alignment of a plurality of nozzles 142 of the applicator arrangement 140 in a distal direction. As shown in FIG. 6, the x-directional axis extends along a width of the distal opening 117, horizontally to the view shown in FIG. 6. The y-directional axis extends along a length of the distal opening 117, vertically to the view shown in FIG. 6. The z-directional axis extends in a direction into and out of the view shown in FIG. 6. The processing arrangement 150 analyzes the image data to identify at least one shadow cast by the grating bars 118 and/or by the outer edges of the protruding portion 114 of the end effector 110. The processing arrangement 150 further analyzes the length, width and/or shape of the shadow to determine each directional component (e.g., in the x, y, and z directions as illustrated in FIG. 6) to the tilt of the device 100. In particular, a tilt about the y-axis will be detected in this embodiment when the shadow appears longer on one side along the x-axis (e.g., left side of the view shown in FIG. 6) as compared to the opposite side of the x-axis (e.g., right side of the view shown in FIG. 6). A tilt about the x-axis can be detected when the shadow appears wider on one side along the y-axis (e.g., towards the bottom of the view shown in FIG. 6) as compared to the opposite side of the y-axis (e.g., towards the top of the view shown in FIG. 6). A size of the shadow, e.g., length and/or width, may be further analyzed to determine a parallel distance of the device from the skin surface, e.g., a distance from the skin surface in the z-direction. The size of the shadow becomes larger as the device is positioned further from the skin surface. In addition, the device may provide feedback to the user suggesting a corrective movement to reduce the tilt. The feedback may be in a direction and to a degree corresponding to a vector opposing that of the tilt of the device.

FIG. 6 shows two separate illustrative examples of shadows 402, 404 cast by the outer edges of the protruding portion 114 of the end effector 110. It is noted that shadows 402, 404 are shown together in FIG. 6 for illustrative purpose only. When the device is in use, shadows 402, 404 are detected by the processing arrangement 150 in image data corresponding to separate images that reflect different directions and degrees of tilt of the device 100, as discussed below. The shadow 402 shown on the left side does not indicate a tilt component in either the x-directional or the y-directional axes. However, the length and width of shadow 402 can be analyzed by the processing arrangement 150 to determine a distance in the z-direction between the device and the skin surface. The shadow 404 shown on the right side indicates a tilt component in a z-direction about the x-axis. As can be seen in FIG. 6, the top portion of the shadow 404 is narrower than the bottom portion of shadow 404 indicating that the device is tilted towards the skin an upward direction along the y-axis and away from the skin in a downward direction along the y-axis.

Furthermore, the grating bars 118 divide the distal opening 117 into a plurality of opening segments 117a, each portion of the area of skin framed by each of the opening segments 117a may be independently analyzed by the processing arrangement 150 to determine, for each segment 117a, whether the corresponding portion of skin is suitable for application of the composition. For example, the processing arrangement 150 analyzes the image data to identify and determine a tilt of each opening segment 117a based on at least one shadow cast by an adjacent grating bar 118 and/or outer edge of the protruding portion 114 of the end effector 110, as discussed above. The processing arrangement 150 identifies and measures the shadows to independently determine whether a nozzle 142 aligned with each opening segment 117a is aimed to safely dispense the composition to an area of skin within the opening segment 117a, and controls operating of the applicator arrangement 140 so that only those nozzles 142 aimed to safely dispense the composition through their corresponding opening segments 117a are permitted to apply the composition to the skin. In contrast, those nozzles 142 aimed through those opening segments 117 to dispense the composition in an unsafe manner to the skin, as assessed by the tilt of each opening segment 117a, are temporarily restricted from applying the composition to the skin so as to individually improve safety of operation for each nozzle 142. This embodiment is further illustrated in Example I below.

Figure 7A:
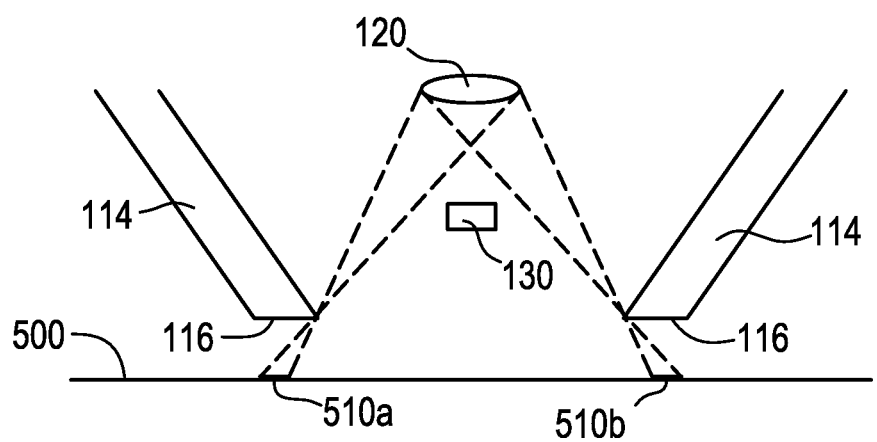
FIG. 7a shows another exemplary embodiment of a protruding portion of an end effector of a device for applying a composition to the skin of a user.
Figure 7B:
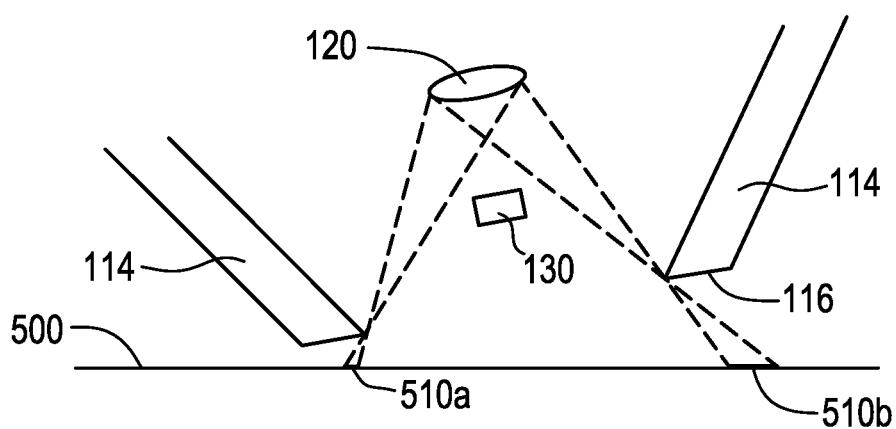
FIG. 7b shows the exemplary embodiment of a protruding portion of an end effector of the device of FIG. 7a in a tilted configuration.

In an alternative embodiment shown in FIGS. 7a and 7b, the processing arrangement 150 analyzes the image data to identify a pair of shadows 510a, 510b cast by at least two of the grating bars 118 and/or by an outer edge of the protruding portion 114 of the end effector 110 and determines a tilt of the device 100 or the nozzle(s) 142 relative to the surface of the skin 500 based on a ratio of the length and/or width of the shadows 510a, 510b. FIGS. 7a and 7b show a side view for an interior of the head portion 104 of the device 100. As shown in FIGS. 7a and 7b, at least one light source 120 is positioned proximal to a sensor of the detector arrangement 130, and the light source(s) 120 and the detector arrangement 130 are positioned at or near a midpoint between opposing outer edges of the protruding portion 114 of the end effector 110. The light source(s) 120 and/or the detector arrangement 130 may be positioned anywhere within the interior of the head portion 104 of the device 100 and may be positioned closer towards one outer edge (e.g., on the left side) as compared to an opposing outer edge (e.g., on the right side), or vice versa. The light source(s) 120 may illuminate an interior of the protruding portion 114 of the end effector 110. As can be seen in FIGS. 7a and 7b, when a distal end 116 of the end effector 110 is not in direct contact with a surface of the skin 500, each of the opposing outer edges of the protruding portion 114 casts a shadow 510a, 510b on the surface of the skin 500. The processing arrangement 150 further analyzes the image data to determine a length and/or a width of each of the shadows 510a, 510b to determine a ratio of the length or width of shadows casted by opposing outer edges of the protruding portion 114. For example, the ratio is between the length or width of the shadow 510a to the length or width of shadow 510b. When the ratio is within a predetermined range, the applicator arrangement 140 (not shown in FIGS. 7a and 7b) is determined to be aimed to safely dispense the composition to the surface of the skin 500. When the ratio between the lengths or widths of the shadows 510a, 510b is outside a predetermined range, the applicator arrangement 140 is determined to be aimed in an unsafe manner. More particularly, if the ratio between the length or width of the shadow 510a to that of the shadow 510b is within a predetermined range, the tilt of the device 100 is determined to be with in an acceptable margin of error for a tilt of the distal end 116 relative to the surface of the skin 500. For example, as shown in FIG. 7a, a ratio of the length of the shadow 510a to that of shadow 510b at or close to 1:1 indicates that the distal end 116 is parallel or substantially parallel to the surface of the skin 500—i.e., not substantially tilted. Therefore, in this particular embodiment, if the ratio of the lengths of the shadows cast by opposing outer edges of the protruding portion 114 is close to or within a desired margin of error to a ratio of 1:1, the applicator arrangement 140 is determined to be aimed to safely dispense the composition to the surface of the skin 500. As can be seen in FIG. 7b, the device 100 is significantly tilted from the surface of the skin 500 such that shadow 510a is significantly shorter than shadow 510b. Therefore, the ratio of the length of the shadow 510a to that of shadow 510b significantly deviates from the 1:1 ratio shown in FIG. 7a indicating that the distal end 116 is positioned at a significant angle to the surface of the skin 500 and the device 100 is determined not to be aimed to dispense the composition in a safe manner.

Although the embodiment shown in FIGS. 7a and 7b is described with respect to shadows cast by opposing outer edges of the protruding portion 114, it is contemplated that the processing arrangement 150 may similarly analyze the image data to identify shadows cast by opposing grating bars 118 framing an opening segment 117a of a distal opening 117 to determine a tilt of nozzles(s) 142 corresponding to the opening segment 117a relative to the surface of the skin 500. Each portion of the area of skin framed by each of the opening segments 117a may be independently analyzed by the processing arrangement 150 to determine, for each segment 117a, a ratio of shadows cast by opposing grating bars 118 framing an opening segment 117 to determine whether the device 100 is oriented for safe application of the composition to the corresponding portion of skin.

Although FIGS. 7a and 7b show a flat portion of skin 500, the ratio of the lengths and/or widths of shadows 510a, 510b cast by opposing outer edges of the protruding portion 114, as described above, may be used to determine a tilt of the device 100 or the nozzle(s) 142 relative to the surface of the skin 500 for skin of any contour. In particular, as discussed above, the contours of the face are generally curved around certain sensitive regions and therefore, as a user attempts to address these areas, the surface of the skin may curve away from the outer edges of the protruding portion 114. Therefore, when the ratio between the lengths of the shadows 510a, 510b is outside a predetermined range, the processing arrangement 150 may determine that the device 100 is overly tilted relative to a surface of the skin 500, or that the device 100 is near or over one of the sensitive regions—either of which may be used as the basis for a determination that the applicator arrangement 140 is not aimed to dispense the composition in a safe manner.

As discussed above, the applicator arrangement 140 is determined to be aimed to safely dispense the composition to the skin, the method 300 proceeds to step 310 in which the image data is further analyzed to identify locations within the area of skin to which the composition should be applied. In this particular embodiment, the image data corresponds to an image or one or more frames of images of an area of skin obtained through a grated end effector 110, and therefore, the image data corresponds to those regions of skin between the grating bars 118 that are visible to the detector arrangement 130, not to the skin underlying the grating bars 118. Therefore, in one embodiment of step 310, the image data may be adjusted so that portions of the image data corresponding to the grating bars 118 are modified by the processing arrangement 150 and the adjusted image data is further analyzed by the processing arrangement 150 to identify locations within the area of skin to which the composition should be applied. Such an adjustment to the image data is particularly useful to those analysis methods that utilize an average or an overall data profile of the imaged area of skin to identify skin artifacts, because the portions of the image data corresponding to the grating bars 118, which is significantly visually different from skin, would otherwise introduce a distortion to the results of such analysis methods. Therefore, the processing arrangement 150 in this embodiment adjusts the image data by substituting for data corresponding to portions of the image including the grating bars 118 with data that approximates portions of the skin not covered by the grating bars 118 in the captured image. For example, the processing arrangement 150 may adjust the image data such that data for portions of the image corresponding to the grating bars 118 is replaced by an average value, e.g., an average reflectance, of the remaining portions of the image. In another example, the processing arrangement 150 may adjust the image data such that data for portions of the image corresponding to the grating bars 118 is replaced by extrapolated values generated based on adjacent regions of the captured image. In a further example, the processing arrangement 150 adjusts the image data using a database of previously obtained image data mapped to regions of the face of the user, where data for portions of the image corresponding to grating bars 118 is replaced by previously obtained image data corresponding to regions of the face covered by the grating bars 118 in the captured image.

EXAMPLE

Example I

In Example I, an exemplary device 100 as described above and illustrated in FIG. 4 includes two separate green LEDs as its first and second light sources 121, 122. The first and second light sources 121, 122 are individually and separately controlled by the processing arrangement 150 to turn on and off independently from each other. In this example, the device 100 determines whether a nozzle (not shown) is aimed to safely dispense a composition to an area of skin to which a first opening segment 206 is positioned over. The first and second light sources 121, 122 may each have a different wavelength and may be turned on simultaneously. Alternatively, the first light source 121 may be turned on while the remainder of the light source(s) 120, 122 are turned off for a predetermined amount of time. The detector arrangement 130 captures one or more frames of images of encompassing the area of skin framed by the first opening segment 206 during this time (e.g., for 100 frames) to generate image data. The processing arrangement 150 analyzes the image data to identify a first shadow 208 cast onto the area of skin framed by the first opening segment 206 by an adjacent grating bar 118 and to determine a length of the first shadow 208. If the length of the first shadow 208 is above a predetermined threshold, then the processing arrangement 150 determines the nozzle to be unsafely aimed to dispense a composition to an area of skin over which the first opening segment 206 is positioned. If the length of the first shadow 208 is below the predetermined threshold, then the processing arrangement 150 determines the nozzle to be safely aimed to dispense the composition to the area of skin over which the first opening segment 206 is placed and allows the device 100 to further proceed with identifying and applying the composition to frexel(s) within the first opening segment 206 at which skin artifacts are detected.

In this example, the device 100 also determines whether an area of skin over which a second opening segment 210 is positioned is safe and/or suitable for application of a composition, independent from the above described imaging and analysis for the first opening segment 206. In a preferred embodiment, the first and second light sources 121, 122 each have a different wavelength and are both used to illuminate the area of skin simultaneously. Alternatively, the first light source 121 may be turned off and the second light source 122 is turned on for another predetermined amount of time. The detector arrangement 130 captures a separate set of image(s) encompassing the area of skin framed by the second opening segment 210 during this second period of time (e.g., for 100 frames) to generate a second set of image data. The processing arrangement 150 analyzes the second set of image data to identify and determine a length of the second shadow 212, in a manner similar to that discussed above for the first shadow 208. If the length of the second shadow 212 is above a predetermined threshold, then the processing arrangement 150 determines that another nozzle (not shown) aimed to dispense the composition to an area of skin framed by the second opening segment 210 in an unsafe manner. If the length of the second shadow 212 is below the predetermined threshold, the processing arrangement 150 determines that the another nozzle is aimed to safely dispense the composition to an area of skin over which the second opening segment 210 is placed and allows the device 100 to further proceed to identify and selectively apply the composition to frexel(s) within the second opening segment 210 at which skin artifacts are detected.

Although Example I describes independent imaging and analysis of two opening segments, it is contemplated that each of the opening segments 117a may be separately imaged and analyzed by the device 100 in a similar manner as described above.

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All publications cited herein are incorporated by reference in their entirety.

What is claimed is:

1. A handheld device for applying a composition to a skin of a face of user, comprising:
    an end effector comprising a base portion and a protruding portion extending distally from the base portion, the protruding portion having a distal opening and further comprises a plurality of grating bars extending across the distal opening;
    a detector arrangement configured to obtain image data corresponding to an image of an area of the skin through the distal opening of the end effector, wherein the image data corresponds to an image of the area of skin overlaid with the plurality of grating bars;

an applicator arrangement configured to apply the composition to a location within the area of the skin; and
a processing arrangement configured to
receive the image data from the detector arrangement,
analyze the image data to determine whether the applicator arrangement is aimed to safely dispense the composition to the area of skin and whether a frexel within the area of skin corresponds to a skin artifact, wherein the processing arrangement determines the applicator arrangement to be aimed to safely dispense the composition to the area of skin when the image data corresponds to a region on the face of the user located at least a predetermined distance away from at least one of eyes, nostrils and mouth of the face of the user, and
direct the applicator arrangement to withhold from application of the composition to the skin when the applicator arrangement is not safely aimed to dispense the composition to the area of skin.

2. The device of claim 1, wherein the processing arrangement analyzes the image data to determine a tilt of the device.

3. The device of claim 2, wherein the processing arrangement determines the applicator arrangement to be aimed to safely dispense the composition to the area of skin when a magnitude of the tilt of the device is below a predetermined threshold, and determines the applicator arrangement as not safely aimed to dispense the composition to the area of skin when magnitude of the tilt of the device is above the predetermined threshold.

4. The device of claim 1, wherein the processing arrangement is configured to analyze the image data to identify a shadow of at least one of the grating bars in the image and determining a length of the shadow based on the image data.

5. The device of claim 4, wherein the processing arrangement is further configured to determine the applicator arrangement to be aimed to safely dispense the composition to the area of skin when the length of the shadow is below a predetermined threshold, and determine the applicator arrangement as not safely aimed to dispense the composition to the area of skin when the length of the shadow is above the predetermined threshold.

6. The device of claim 1, wherein the processing arrangement is configured to adjust the image data to substitute data for portions of the image corresponding to the grating bars with data generated by the processing arrangement that approximate for skin underlying the grating bars, and to analyze the adjusted image data to identify locations within the area of skin that correspond to skin artifacts.

7. The device of claim 1, wherein the processing arrangement determines whether the skin artifact is detected from the frexel based on a reflectance of the area of skin detected in the image.

8. The device of claim 1, wherein the applicator arrangement comprises a nozzle configured to dispense a pressurized pulse of the composition from a reservoir to form a thin layer of the composition on the skin.

9. The device of claim 8, wherein the composition is a cosmetic composition comprising particles of a reflectance modifying agent in a liquid suspension.

10. The device of claim 9, wherein the reflectance modifying agent is titanium dioxide.

11. A method for application of a composition to a skin of a face a user, comprising:
obtaining, by a detector arrangement, image data corresponding to an image of an area of the skin over which a device is placed overlaid with a plurality of grating bars of an end effector of the device;
analyzing, by a processing arrangement, the image data to determine a tilt of the device as compared to the area of the skin by analyzing the image data to identify a shadow of at least one of the grating bars in the image and analyzing the shadow to determine a three-dimensional vector corresponding to the tilt;
determining, by the processing arrangement, whether an applicator arrangement is aimed to safely dispense the composition to the area of skin based on the tilt of the device, wherein the processing arrangement determines the applicator arrangement to be aimed to safely dispense the composition to the area of skin when a magnitude of the tilt of the device is below a predetermined threshold, and determines the applicator arrangement as not safely aimed to dispense the composition to the area of skin when magnitude of the tilt of the device is above the predetermined threshold;
analyzing, by the processing arrangement, the image data to identify locations within the area of skin that correspond to skin artifacts; and
selectively applying, by the applicator arrangement, the composition to the identified locations only when the applicator arrangement is determined to be aimed to safely dispense the composition to the area of skin, wherein the applicator withholds from application of the composition to the skin when the applicator arrangement is not safely aimed to dispense the composition to the area of skin.

12. The method of claim 11, wherein the processing arrangement adjusts the image data to substitute data for portions of the image corresponding to the grating bars with data generated by the processing arrangement that approximate for skin underlying the grating bars and analyzes the adjusted image data to identify locations within the area of skin that correspond to skin artifacts.

13. The method of claim 11, wherein the processing arrangement identifies locations within the area of skin that correspond to skin artifacts based on a reflectance of the area of skin detected in the image.

* * * * *